United States Patent [19]

Saab

[11] Patent Number: 4,820,349

[45] Date of Patent: Apr. 11, 1989

[54] DILATATION CATHETER WITH COLLAPSIBLE OUTER DIAMETER

[75] Inventor: Mark A. Saab, Lawrence, Mass.

[73] Assignee: C. R. Bard, Inc., Murray Hill, N.J.

[21] Appl. No.: 88,098

[22] Filed: Aug. 21, 1987

[51] Int. Cl.$^4$ .............................................. A61M 29/02
[52] U.S. Cl. .................................. 128/344; 604/101; 604/96
[58] Field of Search ................. 128/344; 604/101, 53, 604/96

[56] References Cited

U.S. PATENT DOCUMENTS

| | | | |
|---|---|---|---|
| 4,024,873 | 5/1977 | Antoshkiw | 128/349 |
| 4,307,722 | 12/1981 | Evans | 128/344 |
| 4,318,410 | 3/1982 | Chin | 128/325 |
| 4,323,071 | 4/1982 | Simpson | 128/343 |
| 4,335,723 | 6/1982 | Patel | 604/101 |
| 4,338,942 | 7/1982 | Fogarty | 128/344 |
| 4,351,341 | 9/1982 | Goldberg | 128/348 |
| 4,406,656 | 9/1983 | Hattler | 604/280 |
| 4,444,188 | 4/1984 | Bazell | 128/348.1 |
| 4,467,790 | 8/1984 | Schiff | 128/1 |
| 4,582,181 | 4/1986 | Samson | 128/348.1 |
| 4,597,755 | 7/1986 | Samson | 604/96 |
| 4,616,653 | 10/1986 | Samson | 128/344 |
| 4,670,313 | 6/1987 | Saudagar | 604/96 |
| 4,706,670 | 11/1987 | Andersen et al. | 128/344 |
| 4,715,378 | 12/1987 | Pope, Jr. et al. | 604/96 |
| 4,733,652 | 3/1988 | Kantrowitz | 604/96 |
| 4,771,778 | 9/1988 | Mar | 604/96 |

OTHER PUBLICATIONS

"USCI Gruntzig Dilaca Lo Profile II Bal&oon Dilatation Catheters", No. 1-86/5090043, 1986.

Primary Examiner—E. Rollins Cross
Attorney, Agent, or Firm—Wolf, Greenfield & Sacks

[57] ABSTRACT

A balloon dilatation catheter having a balloon at its distal end includes a distal segment having a collapsible outer diameter. The distal segment includes an inner shaft and a generally coaxial outer surrounding sleeve formed from a very flexible, thin wall, high-strength polymeric material. The balloon is formed integrally with the sleeve and is collapsible about the shaft together with the sleeve. The distal segment of the catheter exhibits a high degree of trackability over a guidewire through tortuous blood vessels. When in its collapsed configuration, the distal segment of the catheter defines a reduced profile which is less obstructive to blood flow through the blood vessel containing the catheter distal segment, such as a coronary artery. In a modified embodiment of the invention, the flexible thin wall sleeve extends over a greater length of the catheter and may extend to the full length of the catheter. In the modified embodiment, when the sleeve is collapsed about the inner shaft a reduced profile is defined along the length of the catheter. When contained within a guide catheter, the dilatation catheter provides for an enlarged cross-sectional flow area within the guide catheter, thus enhancing proximal dye injections and pressure measurements or, alternately, enabling the use of a smaller diameter guide catheter.

19 Claims, 6 Drawing Sheets

DILATATION CATHETER WITH COLLAPSIBLE OUTER DIAMETER

FIELD OF THE INVENTION

The invention relates to improvements in balloon dilatation catheters such as those used in angioplasty procedures and, particularly percutaneous transluminal coronary angioplasty.

BACKGROUND OF THE INVENTION

In recent years there has been a substantial increase in the use of percutaneous transluminal angioplasty for the treatment of vascular stenoses and, particularly, stenoses of the coronary arteries. The use of balloon dilatation catheters for such angioplasty procedures may provide for many patients an effective alternative to coronary artery bypass surgery.

In a typical coronary angioplasty procedure, a guide catheter is introduced into the patient's arterial system through the femoral artery and is advanced through the aorta and to the ostium of the coronary artery. Once the guide catheter is positioned with its tip intubated in the coronary ostium, a balloon dilatation catheter which typically will have been fitted with a small diameter guidewire, such as the steerable guidewire disclosed in U.S. Pat. No. 4,453,930, is advanced through the guide catheter to and into the coronary artery. Once the dilatation catheter and steerable guidewire are located in the coronary arterial tree, the catheter is positioned by manipulations of the catheter and the guidewire in which the distal tip of the guidewire is selectively steered through the branches and tortuous passages of the arterial anatomy and with dilatation catheter being advanced over the guidewire after the guidewire is positioned. When the balloon is positioned in the stenosis, it is inflated under pressure to effect the dilatation, thereby, forcably enlarging the narrowed lumen of the artery.

Among the desirable features of the dilatation catheter is that it should be highly flexible so that it can track easily along the guidewire through sharp bends and tortuous coronary arteries. If the catheter is too stiff, it will not track well and instead of following the natural contour of the artery and flexible guidewire, it will tend to straighten the artery which causes it to press against the arterial walls as well as the guidewire which, in turn, presents difficulty in manipulating and positioning the guidewire and catheter. Another difficulty encountered with balloon dilatation catheters is that the presence of the catheter in the artery presents an obstruction to blood flow in the artery. Where the angioplasty procedure is performed in arteries that are already suffering from narrowing stenoses, the presence of the catheter during the angioplasty procedure itself presents an obstruction and somewhat of an increased risk of ischemia in distal portions of the artery. It is among the general objects of the invention to provide an improved dilatation catheter that displays superior trackability and also minimizes the degree of obstruction within the artery.

The angioplasty procedure typically includes the periodic injection of radiopaque dyes into the coronary arterial tree to enable the physician to observe, fluoroscopically, the conditions of the coronary anatomy during the procedure as well as to visualize the anatomy to help in positioning the dilatation catheter. It also is among the common procedures to make measurements of the blood pressure both proximally and distally of the stenosis to compare the pressure gradient in the artery before the dilatation with the pressure gradient after dilatation. Ideally, the dilatation procedure enlarges the arterial obstruction thereby reducing the pressure gradient along that region. The observation of a reduced pressure gradient signifies that the dilatation procedure is accomplishing its objective and is an important feature to be monitored by the physician. Typically, the guide catheter, the tip of which is in communication with the cornary ostium, is used to inject dye into the coronary arterial tree as well as to make pressure measurements on the proximal side of the stenosis. In order to obtain enhanced dye injections and pressure measurements, it is desirable that the cross-sectional flow area through the guide catheter be as large as possible. However, it also is desirable to maintain a reduced diameter for the guide catheter so that it will be more easily inserted into the patient and so that the distal end of the guide catheter may be more securely intubated into the coronary ostium. It is among the general objects of the invention to provide a modified dilatation cathether which achieves these objectives.

Thus, it is among the general objects of the invention to provide a novel dilatation catheter construction which displays superior tracking and a low profile for the balloon as well as for the distal segment of the catheter and which provides other significant advantages over prior diliation catheters.

SUMMARY OF THE INVENTION

The catheter includes a flexible shaft having proximal and distal segments. A main lumen and an inflation lumen extend through the shaft. The distal segment of the shaft is of reduced diameter. The inflation lumen terminates at the juncture of the proximal and distal segments of the shaft. The distal segment of the shaft is surrounded by a sleeve formed from a very thin, flexible and strong polymeric material such as highly oriented polyethylene terephthalate and the dilatation balloon is formed integrally with the sleeve. The proximal end of the sleeve is attached to the distal portion of the proximal segment of the shaft so that the inflation lumen is in communication with the interior of the sleeve. The distal end of the sleeve is attached to the distal region of the distal segment of the catheter shaft. Both the sleeve and the balloon are extremely flexible and both are collapsible about the shaft in response to application of a negative pressure to the inflation lumen. The thin flexible wall of each of the sleeve and balloon enable them to collapse closely against the smaller diameter of the distal segment of the shaft thereby providing a reduced profile for the distal segment of the catheter when the catheter is in the deflated mode. The very thin wall of the sleeve presents negligible bending resistance and enables the distal segment of the catheter to have an extremely high degree of flexibility and superior ability to track over a guidewire even in sharply curved or tortuous blood vessels. Additionally, the low profile of the distal segment of the catheter when the sleeve is collapsed provides for reduced obstruction and increased cross-sectional flow area within the coronary artery in which the catheter is placed.

In the foregoing embodiment of the invention, the distal segment extends over a length of the order about ten to fifteen centimeters, a distance sufficient to reach the distal extremities of the coronary arterial tree without extending any portion of the proximal region of the catheter shaft out of the guide catheter. In a modified embodiment of the invention, the collapsible sleeve extends over a greater distance along the catheter and may extend fully to the proximal end of the catheter. In the modified embodiment, the outer diameter of the catheter thus is collapsible substantially to the smaller diameter of the shaft to provide an increased annular flow area between the dilatation catheter and the guide catheter. The increased flow area inables improved dye injection capability through the guide catheter while the dilatation catheter is in place and also provides for improved pressure measurement through the guide catheter, proximally of the balloon. Alternately, the modified embodiment of the dilatation catheter enables the use of a guide catheter having a smaller diameter without reducing the annular flow area through the guide catheter. The use of a smaller guide catheter has advantages in that it is more easily placed and positioned in the patient and reduces the size of the entry site which decreases bleeding and reduces recovery time after the procedure.

It is among the general objects of the invention to provide an improved balloon dilatation catheter.

Another object of the invention is to provide a dilatation catheter having superior tracking ability.

A further object of the invention is to provide a dilatation catheter which has a sufficient stiffness in its proximal segment so that it may be easily pushed over a guidewire yet which displays a high degree of flexibility in its distal segment for superior tracking.

A further object of the invention is to provide a dilatation catheter that provides less obstruction to the artery when in a deflated mode.

Another object of the invention is to provide a dilatation catheter which enables use of a smaller diameter guide catheter.

A further object of the invention is to provide a dilatation catheter that enables improved proximal dye injection and pressure measurement to be made through a guide catheter, through which the dilatation catheter extends.

Another object of the invention is to provide a dilatation catheter having an inner shaft portion and an outer tubular sleeve surrounding the inner shaft portion and in which the outer tubular portion is collapsible about the inner shaft in response to negative pressure applied to the sleeve.

Another object of the invention is to provide an improved catheter adapted for use in percutaneous translumenal angioplasty of the coronary arteries.

Another object of the invention is to provide a catheter which enables the practice of an improved method of angioplasty and, particularly, angioplasty of the coronary arties.

DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENT

Figure 1:
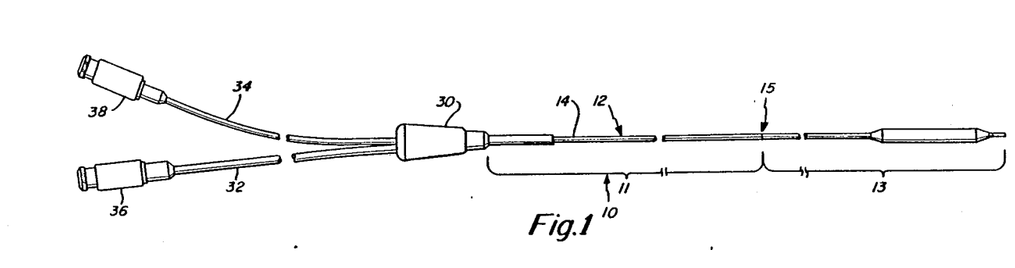
FIG. 1 is a fragmented illustration of the catheter.

The balloon dilatation catheter is indicated generally at 10 in FIG. 1 and may be considered as having a proximal segment 11 and a distal segment 13. The catheter includes a shaft 12 which may be extruded from an appropriate polymer such as polyvinyl chloride or polyethylene. The shaft 12 includes a main, proximal portion which may be considered as having a full diameter 14 and a distal shaft extension 16 of a smaller diameter. The proximal shaft portion 14 has a main lumen 18 formed therethrough which continues through the distal shaft segment 16, the main lumen 18 terminating at a distal outlet 20 at the distal tip of the catheter. The proximal shaft portion 14 also is provided with an inflation lumen 22 having a smaller cross-sectional area, the inflation lumen 22 terminating at the region of the transition 15 of the proximal segment 11 to the distal segment 13. A sleeve 24 formed from a thin, highly flexible, high-strength polymeric material, as will be described, extends over the distal segment 13 of the catheter, and encloses the distal shaft extension 16. The proximal end of the sleeve 24 is adhesively attached to the proximal shaft portion 14 in the transition region 15 adjacent the distal end of the inflation lumen 22 and is substantially the same outer diameter as the proximal shaft portion 14. The distal end of the sleeve 24 is formed to define a reduced diameter neck 26 which is adhesively attached to the distal portion of the distal shaft extension 16.

Figure 2:
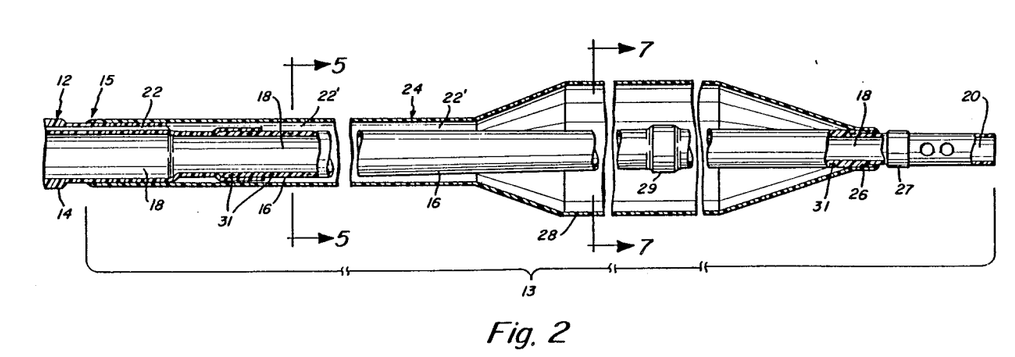
FIG. 2 is an enlarged sectional fragmented section of the distal region of the catheter.

A tip marker 27 which may be formed from a band or coil of radiopaque material preferably is mounted on the distal tip of the shaft extension 16. An additional radiopaque marker band 29 may be mounted on the distal shaft extension 16 within the region of the balloon to indicate the position of the balloon fluoroscopically during the dilatation procedure. It may be noted that the shaft extension 16 may be reinforced with an internally embedded helical coil 31 that extends along the shaft extension 16 to reinforce the shaft extension 16 and prevent it from collapsing under the pressures developed during the dilatation procedure. The coil 31 may be embedded in the shaft extension 16 by forming shaft extension from a pair of tubes of plastic (such as polyvinylchloride) with the coil 31 placed between the tubes. The tubes then may be fused together with the coil 31 being embedded in the material. The balloon marker 29 also may be attached in the same manner.

The distal region of the sleeve 24 is formed to define an enlarged diameter dilatation balloon 28. The dilatation balloon 28 may be inflated and deflated by applying positive or negative fluid pressure through inflation lumen 22 and the generally annular continuation of the inflation lumen 22. As will be described in further detail, both the balloon 28 and the proximal portion of the sleeve 24 are collapsible about the smaller diameter distal shaft extension 16 when negative pressure is applied to the inflation lumen 22.

As shown in FIG. 1, the catheter shaft 12 is provided, at its proximal end, with a bifurcated fitting 30 from which a pair of tubular legs extend, including a main lumen leg 32 which communicates with the main lumen 18 of the catheter and an inflation lumen leg 34 which communicates with the inflation lumen 22 of the catheter. Each of the legs 32, 34 is provided with a luer connector 36, 38 respectively for connection to various adaptors, syringes, inflation devices and the like.

Figure 3:
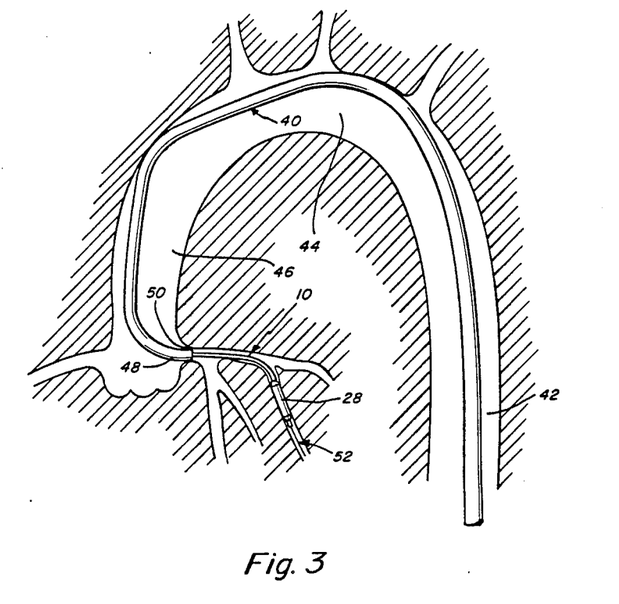
FIG. 3 is a diagrammatic illustration of the coronary anatomy with a guide catheter, a dilatation catheter and small diameter steerable guidewire extending through the anatomy.

FIG. 3 illustrates, diagrammatically, the manner in which a dilatation catheter is used with a guide catheter 40 and a small diameter steerable guidewire 52 to place the dilatation catheter 10 in a selected branch of the coronary arterial tree. FIG. 3 illustrates the guide catheter 40 as having been placed so as to extend through the aorta 42 and aortic arch 44 and downwardly through the ascending aorta 46 with the distal tip 48 of the guide catheter 40 intubated in the selected coronary ostium 50 at the base of the coronary arterial tree. With the guide catheter 40 so positioned a dilatation catheter 10, having a guidewire 52 in its main lumen 18 with its distal tip protruding distally beyond the distal tip of the catheter 10, is dvanced through the guide catheter 40 and beyond the distal tip 48 into the coronary artery. The physician may inject radiopaque dye through the guide catheter 40 into the coronary arteries to visual them on a fluoroscope and also may measure the patient's blood pressure proximally of the balloon 28. The physician also may inject radiopaque dye from the distal end of the dilatation catheter 10 and also may make distal pressure measurements through the main lumen 18 of the dilatation catheter 10. In accordance with the present invention, the distal segment 13 and sleeve 24 of the dilatation catheter are sufficiently long so that even when the distal end of the dilatation catheter is extended as far as possible into the coronary arterial tree, the transition region 15 remains inside of the guide catheter 40.

In accordance with the invention, the sleeve 24 and balloon 28 are formed to be very thin and highly flexible yet sufficiently strong to withstand the pressures developed during dilatation without excessive compliance. In the preferred embodiment of the invention, the sleeve 24 and balloon 28 are formed in a single integral piece from polyethylene terephthalate (PET). By way of example the sleeve 24, including the balloon 28, may be between 10 to 15 centimeters long. For a balloon diameter of the order of 3 millimeters, and a burst pressure of about 15 atmospheres, the balloon 28 may have a wall thickness of the order of 0.0002 inches and a length of about 20 millimeters. The portion of the sleeve 24 proximally of the balloon 28 may have a diameter in the order of 0.053 inches, a wall thickness of 0.0005 inches and a length of about ten to thirteen centimeters.

Figure 4:
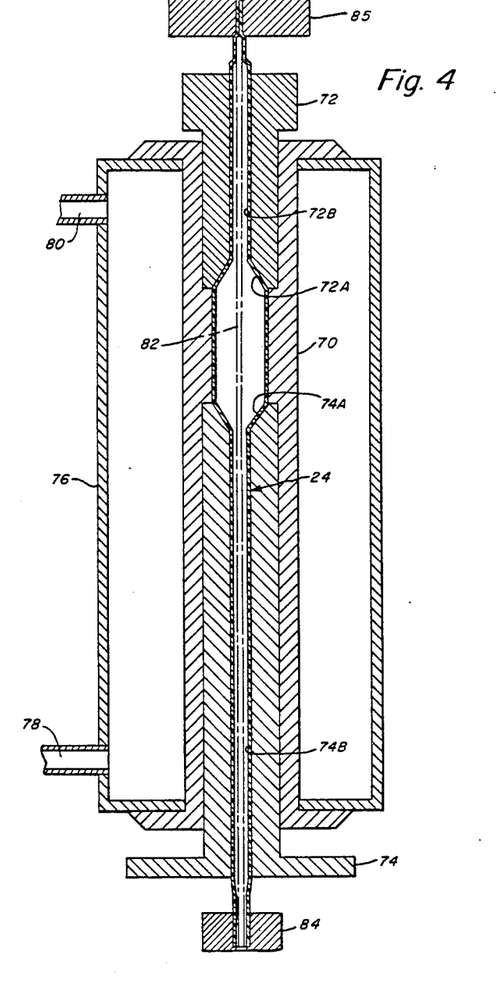
FIG. 4 is a diagrammatic illustration of the mold used in making the integral sleeve and balloon used in the invention.

The integral balloon and sleeve may be formed using methods described in copending application Ser. No. 001,759 filed Jan. 9, 1987 entitled Thin Wall High Strength Balloon and Method of Manufacture which describes the use of high-stretch ratios and heat setting to provide balloons having surprisingly thin, flexible and strong properties. Balloons made in accordance with the techniques described in that application are characterized by a wall thickness to diameter ratio of less than $5.0 \times 10^{-3}$. Typically, such balloons may have a radial tensile strength greater than about 35,000 psi. For example, in order to form the illustrative integral balloon and sleeve described above a mold, as illustrated in FIG. 4 may be used. The mold as shown in FIG. 4 includes a mold body 70 having an internal bore which defines the intended dimension of the finished balloon and sleeve. The mold also includes a pair of end members including a fixed end member 74 and a movable end member 72. Both end members include outwardly tapering portions 74A, 72A respectively, which merge into smaller diameter end bores 74B, 72B respectively. A water jacket 76 having inlet and outlet ports 78, 80 surrounds the mold 70. The mold parts are formed from a material such as brass having good heat conductivity.

The mold 70 receives a tubular parison indicated in phantom at 82 in FIG. 4. The parison is gripped at its ends which extend outwardly of the mold, one of the ends of being sealed and the other end being connected securely to a source of fluid (such as gas) under pressure as by a fitting 84. The clamp 85 and fitting 84 are mounted, by means not shown, to enable them to be drawn upon axially so as to impart an axial stretch to the parison 82.

The parison is formed from a polymer such as PET and its dimensions are selected with respect to the intended final configuration of the balloon to result in the balloon having the desired properties and dimensions, as described more fully in application Ser. No. 001,759, reference being made to said application for full details of the procedure.

It should be noted that the parison is thin walled and after stretching is highly oriented, being stretched radially close to the elastic limit of the material at the inner surface of the tube. Orientation takes place at an elevated temperature that is controlled by a heat transfer of fluids circulated through the water jacket. The parison is drawn axially and then, while being so drawn is expanded radially within the mold. The orientation takes place at a temperature between the first and second order transition temperatures of the material, preferably at about 90° C. for the PET material. For the 3.0 millimeter diameter balloon of the illustrative embodiment, the starting parison may be a tube of PET having inner diameter of 0.429 millimeters and an outer diameter of 0.638 millimeters. The parison may be stretched axially to about 3.1 times its original length. During the axial stretching the parison is expanded radially by admitting gas under pressure into the tubular parison through fitting 84 to stretch the parison to the enlarged diameters as determined by the mold members. After the parison has been radially enlarged to the diameters of the mold the balloon pressure is released and the longitudinal stretching at both ends of the parison is continued. Then the short end of the parison (contained in the movable mold member 72) is held stationary and the long end of the parison (held within fixed mold member 74) is continually drawn to continue to stretch the long portion of the parison that will become the elongate proximal portion of the sleeve 24 of the present invention. After the axial stretching has been completed the stretched and expanded balloon and sleeve is repressurized and is then subjected to a heat setting step in which steam is circulated through the jacket 76 at a temperature above the stretching temperature and is maintained for a time sufficiently to increase the degree of crystalinity in the material. After the heat setting step the mold is cooled to a temperature less than the second order transition temperature of the material and the balloon and integral sleeve may be removed from the mold. Preferably, the illustrative embodiment of the invention is made using an internal diameter stretch ratio of 7 and an outer diameter stretch ratio of about 4.7 for the balloon. Preferably the portion of the sleeve proximal of the balloon has an ID stretch ratio of about 3.1 and an OD stretch ratio of about 2.1.

The catheter having the foregoing construction displays a sleeve 24 that is extremely flexible, thin walled and very strong. The sleeve presents minimal resistance to bending which results in a highly flexible distal segment 13 of the catheter. The degree of flexibility is such that the entire sleeve is easily collapsible about the distal shaft extension 16.

Figure 5:
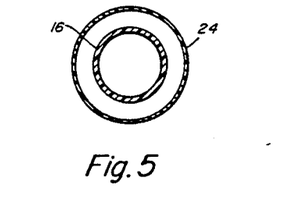
FIG. 5 is a sectional illustration through the catheter with the sleeve and balloon in an expanded configuration as seen along the line 5—5 of FIG. 2.
Figure 6:
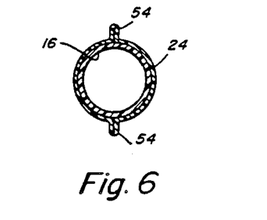
FIG. 6 is an illustration of the sleeve similar to FIG. 5 with the sleeve collapsed about the catheter shaft.
Figures 7, 8:
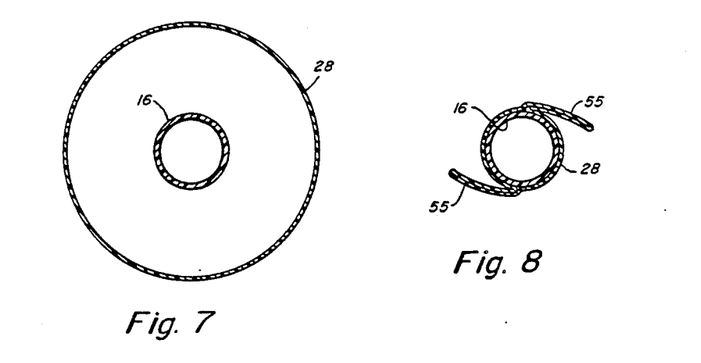
FIG. 7 is a sectional illustration of the balloon as seen along the line 7—7 of FIG. 2 with the balloon in an expanded configuration.
FIG. 8 is an illustration similar to FIG. 7 but with the balloon in a collapsed configuration.

FIGS. 5 and 6 illustrate, respectively, the expanded and collapsed configurations of the proximal portion of the sleeve 24 and FIGS. 7 and 8 similarly illustrate the expanded and collapsed configurations of the balloon portion 28. As shown in FIG. 6 the sleeve 24 is collapsed closely about the distal shaft extension 16 and defines a diameter that is effectively the same as that of the distal shaft extension 16. When collapsed the sleeve 24 forms one or two wings 54 which do not present any significant obstruction to blood flow when the device is in an artery. Thus, when the distal segment 13 of the catheter is disposed within the coronary arterial tree and while the catheter is maintained in its collapsed configuration, the obstruction to blood flow through the coronary artery containing the catheter is reduced and blood perfusion is enhanced. FIG. 8 illustrates the configuration of the collapsed balloon 28. Because the balloon is larger in diameter, it usually will tend to form a pair of very thin wings 55 that may tend to fold over each other, as illustrated.

Figure 9:
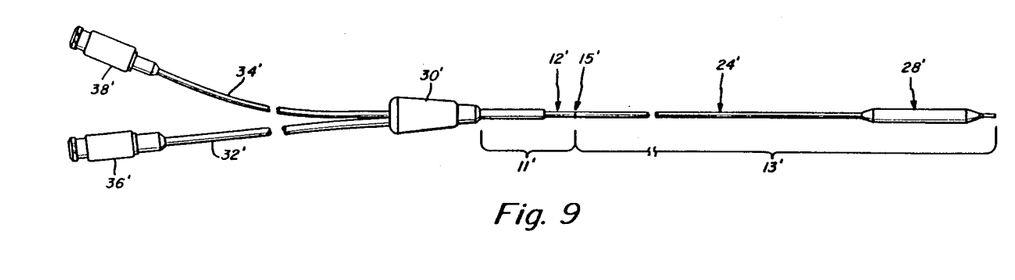
FIG. 9 is an elongated fragmented illustration of a modified embodiment of the invention in which the sleeve extends substantially the full length of the catheter.

FIG. 9 illustrates a modified embodiment of the invention which differs in that the sleeve 24' extends over the full length, or nearly the full length, of the catheter. In this embodiment, the full diameter shaft 12' may be relatively short and may make a transition to a smaller diameter single lumen shaft near the proximal end of the catheter. In this embodiment, the sleeve 24' is joined at transition region 15' to the full diameter shaft and extends over a length that is coextensive with a substantial length of the guide catheter 40 with which the dilatation catheter is to be used. Thus, the distal segment 13' of this embodiment is substantially longer than in the embodiments of FIG. 1.

Figure 10:
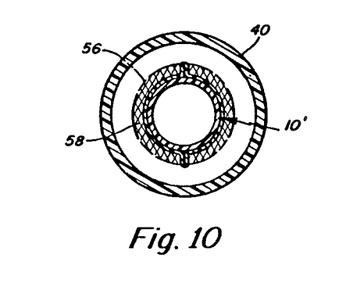
FIG. 10 is a diagrammatic cross-sectional illustration of the modified embodiment of the catheter within a guide catheter and depicting the increased cross-sectional flow area within the guide catheter provided by the invention.

FIG. 10 illustrates, diagrammatically, how the modified form of the invention provides for increased cross-sectional flow area through the guide catheter. The figure illustrates, in solid, the cross-sectional flow area through the generally annular region between the guide catheter 40 and the dilatation catheter 10' (in solid). The circle indicated in phantom at 56 illustrates the normal outer diameter of a conventional non-collapsible dilatation catheter. The increased flow area achieved with the present invention is represented by the cross-hatched area 58.

Figure 11:
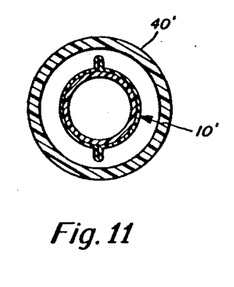
FIG. 11 is a diagrammatic cross-section illustration of the modified embodiment of the invention illustrating the manner in which it may be used with a smaller diameter guide catheter.

FIG. 11 illustrates the manner in which the invention may be employed to use a smaller diameter guide catheter 40'. In those cases where it is adequate to maintain approximately the conventional cross-sectional flow area between the guide catheter 40' and dilatation catheter, the collapsibility of the dilatation catheter enables the required cross-sectional flow area to be achieved within the confines of a smaller diameter guide catheter 40'. The use of a smaller diameter guide catheter provides a number of advantages in that it can be inserted percutaneously into the patient through a smaller opening in the patient's blood vessel and it also is more easily and more securely intubated into the coronary ostium.

Thus, from the foregoing it will be appreciated that the invention provides an improved catheter construction having superior flexibility and trackability. Additionally, the collapsibility of the outer diameter of the catheter provides for improved blood perfusion through the coronary arteries. Moreover, the invention may be incorporated in a catheter so as to provide increased cross-sectional flow area when used with a conventional guide catheter or, alternatively, enables the use of a smaller diameter guide catheter.

It should be understood, however, that the foregoing description of the invention is intended merely to be illustrative thereof and that other modifications and embodiments may be apparent to those skilled in the art without departing from its spirit.

Having thus described the invention, it is desired to claim and secure by Letters Patent:

1. A dilatation catheter comprising:
   an elongated flexible shaft having a proximal segment and a distal segment, the distal segment of the shaft being smaller in diameter than the proximal segment of the shaft;
   the proximal segment having an inflation lumen extending therethrough;
   a sleeve extending over the distal segment of the shaft, the proximal end of the sleeve being attached to the shaft and being in communication with the inflation lumen;
   the distal end of the sleeve being attached to the distal end of the shaft;
   the sleeve having an integral enlarged diameter balloon portion, both the balloon and the sleeve being formed from a thin walled, flexible material and being inflatable and deflatable, both the sleeve and balloon being collapsible about the shaft in response to a negative pressure applied to the inflation lumen,
   whereby the diameter of the catheter in the region of the sleeve may be made to conform closely to the smaller reduced diameter of the distal segment of the shaft.

2. A dilatation catheter as defined in claim 1 wherein said balloon has a wall thickness to outer diameter ratio of less than about $5.0 \times 10^{-3}$.

3. A dilatation catheter as defined in claim 1 wherein the wall thickness of the sleeve is substantially less than the wall thickness of the shaft.

4. A dilatation catheter as defined in claim 1 wherein the sleeve and the balloon are formed from a single unitary piece of polymeric material.

5. A dilatation catheter as defined in any of claims 1 to 4 wherein the proximal segment extends over most of the length of the dilatation catheter and the distal segment extending over a relatively short portion of the overall length of the catheter.

6. A dilatation catheter as defined in claim 5 wherein the distal segment is between about 10 to 15 centimeters in length.

7. A dilatation catheter as defined in claim 5 further comprising a main lumen extending through the shaft and being open at the distal end of the shaft, and means at the proximal end of the catheter for communicating with the main lumen.

8. A dilatation catheter as defined in any of claims 1 to 4 wherein the proximal segment extends over a relatively short portion of the catheter and the distal segment extends over a relatively long portion of the catheter.

9. In combination, a dilatation catheter as defined in claim 8 and a guide catheter, the dilatation catheter being receivable within the guide catheter, whereby when the dilatation catheter is deflated, the combination defines a fluid flow area greater in cross-section than that defined between the proximal shaft portion of the dilatation catheter and the internal lumen of the guide catheter.

10. A dilatation catheter as defined in any of claims 1 to 4, the catheter being dimensioned to be insertable into the coronary arteries to enable the catheter to be used in performance of angioplasty of the coronary arteries.

11. A method for performing angioplasty in an artery comprising,
providing a catheter having a proximal segment and a distal segment, the distal segment including a thin walled, flexible sleeve having an integral enlarged diameter balloon portion formed integrally therewith,
said sleeve and balloon being inflatable and deflatable being collapsible to a smaller diameter when collapsed;
inserting at least the distal segment of the catheter into the blood vessel while maintaining the catheter in said collapsed configuration; and
thereafter inflating the balloon portion.

12. A method of defining claim 11 further comprising;
said catheter being provided with a main lumen adapted to receive a guidewire;
said catheter having a guidewire extending through its main lumen when the catheter is inserted into the artery;
manipulating the guidewire and the catheter in the artery to position the balloon within the artery;
said manipulation being effected while maintaining the sleeve and balloon in a collapsed configuration.

13. A dilatation catheter as defined in claim 5, the catheter being dimensioned to be insertable into the coronary arteries to enable the catheter to be used in performance of angioplasty of the coronary arteries.

14. A dilatation catheter as defined in claim 6, the catheter being dimensioned to be insertable into the coronary arteries to enable the catheter to be used in performance of angioplasty of the coronary arteries.

15. A dilatation catheter as defined in claim 7, the catheter being dimensioned to be insertable into the coronary arteries to enable the catheter to be used in performance of angioplasty of the coronary arteries.

16. A dilatation catheter as defined in claim 8, the catheter being dimensioned to be insertable into the coronary arteries to enable the catheter to be used in performance of angioplasty of the coronary arteries.

17. A dilatation catheter as defined in claim 9, the catheter being dimensioned to be insertable into the coronary arteries to enable the catheter to be used in performance of angioplasty of the coronary arteries.

18. A dilatation catheter comprising:
an elongate flexible supporting shaft having an inflation lumen extending therethrough;
an elongate sleeve extending over the supporting shaft, the sleeve having an integral enlarged diameter balloon portion at its distal region, both the balloon and the sleeve being formed from a thin walled flexible material and being inflatable and deflatable, both the sleeve and the balloon being collapsible about the supporting shaft in response to a negative pressure applied to the inflation lumen.

19. A dilatation catheter as defined in any of claims 1 to 4, 15 or 18 wherein the wall thickness of the sleeve and the balloon is no greater than about 0.0005" thick.

* * * * *